United States Patent [19]
Ricknert

[11] Patent Number: 5,273,491
[45] Date of Patent: Dec. 28, 1993

[54] SEALING AND BEARING ARRANGEMENT IN ELECTRICAL TOOTHBRUSHES

[75] Inventor: Rune Ricknert, Saltsjöbaden, Sweden

[73] Assignee: Ricknert Konsult och Invest Aktiebolag, Saltsjöbaden, Sweden

[21] Appl. No.: 784,413
[22] PCT Filed: Jun. 11, 1990
[86] PCT No.: PCT/SE90/00403
§ 371 Date: Dec. 18, 1991
§ 102(e) Date: Dec. 18, 1991
[87] PCT Pub. No.: WO91/00066
PCT Pub. Date: Jan. 10, 1991

[30] Foreign Application Priority Data

Jun. 30, 1989 [SE] Sweden .................... 8902385-7

[51] Int. Cl.⁵ .................... F16D 3/84; F16C 19/18
[52] U.S. Cl. .................... 464/178; 384/453; 384/512
[58] Field of Search ........... 464/178; 384/512, 515, 384/516, 453, 477, 484; 15/23, 24

[56] References Cited

U.S. PATENT DOCUMENTS

| | | | |
|---|---|---|---|
| 613,712 | 11/1898 | Parkin | 384/477 |
| 678,967 | 7/1901 | Mott | 15/29 |
| 1,697,046 | 1/1929 | Chapman et al. | 464/178 X |
| 1,881,129 | 10/1932 | Peek | 15/29 |
| 1,967,163 | 7/1934 | Thearle | 464/178 X |
| 3,125,383 | 3/1964 | Stahlecker et al. | 384/512 |
| 3,524,088 | 8/1970 | Ryckman, Jr. | 15/22.1 X |
| 4,215,907 | 8/1980 | Pohl | 384/512 |
| 4,504,099 | 3/1985 | Miki et al. | 464/178 X |

FOREIGN PATENT DOCUMENTS 317949 12/1969 Sweden .

Primary Examiner—Daniel P. Stodola
Assistant Examiner—William G. Battista, Jr.
Attorney, Agent, or Firm—Kane, Dalsimer, Sullivan, Kurucz, Levy, Eisele and Richard

[57] ABSTRACT

A sealing and bearing arrangement in electric toothbrushes is characterized by a sealing ring (9) for preventing foreign material from penetrating into a bearing space, the ring being arranged around a nose pin (1) in the open end (7) of a casing (5), which coaxially surrounds the nose pin (1), and being immobile when the nose pin (1) rotates; an annular supporting plate (10) which is provided close to and inwardly of the sealing ring (9) and which is immobile when the nose pin (1) rotates; and bearing balls (11) provided in two races, one on each side of a thickened portion (4) of the central member of the nose pin (1), for taking up forces in all directions.

5 Claims, 2 Drawing Sheets

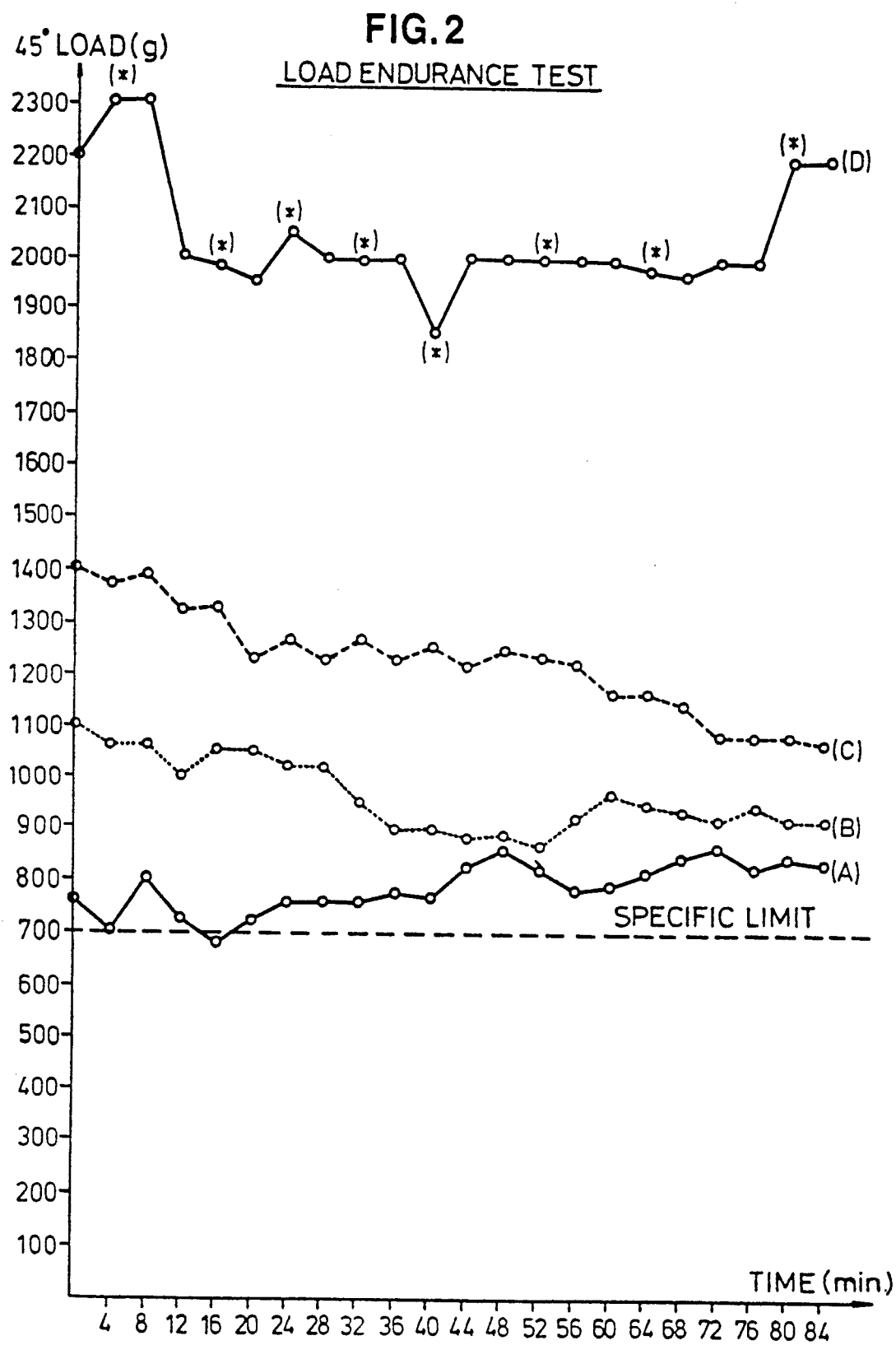

SEALING AND BEARING ARRANGEMENT IN ELECTRICAL TOOTHBRUSHES

BACKGROUND OF THE INVENTION

1. Field of the Invention

The present invention relates to a sealing and bearing arrangement in electric toothbrushes comprising a cylindrical, rotatable nose pin which has a front member on which the brush is to be mounted, a rear member with a means transmitting power from a motor, and a central member partly consisting of a thickened portion; and a hollow casing which is immobile when the nose pin rotates and which coaxially encompasses the central member, including said thickened portion, and whose front end is open, while its rear end sealingly ecompasses the nose pin, there being a clearance between the inner surface of the casing and the central member of the nose pin.

2. Description of the Prior Art

Electric toothbrushes have been on the market for many years, and a plurality of differently functioning designs have gradually been developed. However, many of these are disadvantageous in one respect or the other, e.g. by having too short a service life.

A usual incovenience is that the front member, on which the brush for brushing the teeth and the gums is mounted, is not sufficiently sealed off. Thus, foreign unwanted material, e.g. water, saliva, blood, and toothpaste ingredients, such as pumice, may penetrate into and damage the interior of the toothbrush.

Present-day electric toothbrushes with rotating brushing action comprise a casing which coaxially encompasses a central thickened portion of a rotatable nose pin which drives and rotates the brush. Between the inner surface of the casing and the outer surface of the thickened portion, there is a slide bearing space containing a lubricant. A rubber O-ring is provided in the front end of the casing to prevent foreign material from penetrating into the slide bearing space. However, the sealing action of the O-ring is inadequate. When foreign material penetrates into the slide bearing space, the friction increases, resulting in that heat is generated, the lubricant dries, and wear arises. The toothbrush simply functions so badly that it stalls from time to time and finally stops working at all. Furthermore, lubricant may escape in both directions from the leaky bearing space, and the loss of lubricant may also cause the above-mentioned inconveniences.

Another inconvenience is that the bearing of the toothbrush is not sufficiently strong to withstand the severe, differently directed loads to which it is subjected during teeth brushing. Adjacent to the rear edge of the thickened portion, an annular collar is provided around the nose pin to serve as a hold-up means for the casing and to take up axial forces. The collar is maintained in place by an annular bronze plate arranged around the nose pin, adjacent to the rear edge of the collar. The contact between the collar and the casing has a certain braking effect with ensuing wear. Also, the friction between the mutually adjacent surfaces of the collar and the bronze plate contributes to this braking effect and ensuing wear. The wear also entails a disagreeable squeaking noise and gradually impairs the function of the bearing.

Consequently, there is need for an electric toothbrush with rotating brushing action, which is sealed against unwanted materials and which is mounted in bearings adapted to take up considerable forces in all directions.

SUMMARY OF THE INVENTION

The object of the present invention is to obviate the above inconveniences by providing an improved electric toothbrush.

This object is achieved by means of the combined sealing and bearing arrangement according to the invention, which shows the distinctive features stated in the appended claims.

The combined sealing and bearing arrangement according to the invention gives an electric toothbrush which is more durable and affords a much higher sealing action than known electric toothbrushes. The inventive bearing arrangement can withstand heavier loads, which makes it possible to clean the teeth and the gums more efficiently. Furthermore, it allows a larger space for the lubricant and, consequently, a larger amount of lubricant for the bearing, thus improving the function and sealing factor thereof.

BRIEF DESCRIPTION OF THE DRAWINGS

The invention will now be described in more detail, reference being has to the accompanying drawings, in which FIG. 2 is a diagram illustrating the load as a function of time in a load endurance test carried out with four different toothbrushes.

DETAILED DESCRIPTION OF PREFERRED EMBODIMENT

Figure 1:
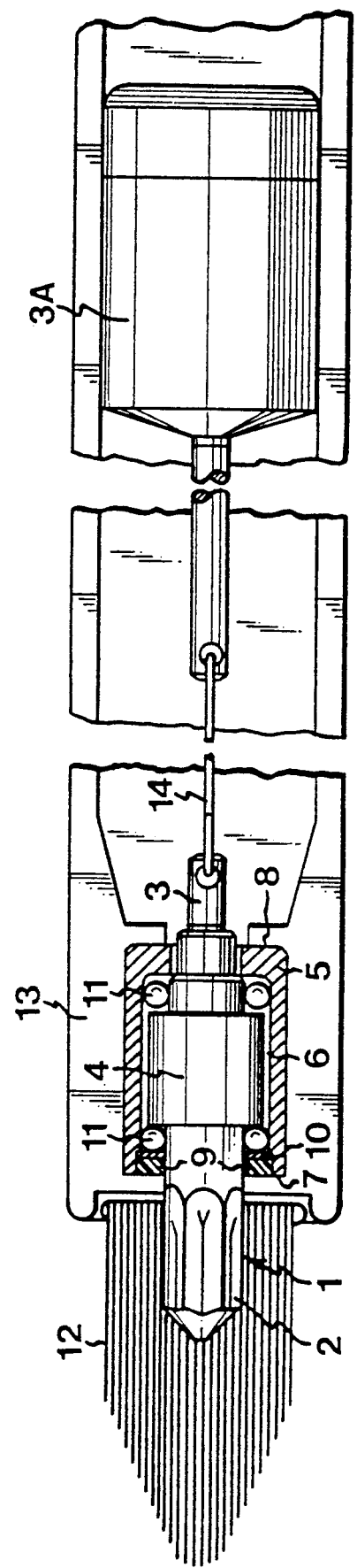
FIG. 1 illustrates the sealing and bearing arrangement according to the invention, as it is adapted to be enclosed in the front member of an electric toothbrush

As shown in FIG. 1, a cylindrical, rotatable nose pin 1 has a front member 2 on which the brush 12 is mounted, a rear member 3 connected, via a power-transmitting means 14, to a motor 3A, and a central member partly consisting of a thickened portion 4. Between the thickened portion 4 and the rear member 3, the diameter of the nose pin 1 is reduced by steps, as shown in the drawing. A hollow casing 5, which is immobile when the nose pin 1 rotates, coaxially encompasses the central member, including the thickened portion 4 of the nose pin 1. The front end 7 of the casing 5 is open, while its rear end 8 closely surrounds the nose pin 1. Between the inner surface of the casing 5 and the thickened portion 4, there is a clearance 6 adapted to accommodate lubricant. A sealing ring 9 is arranged around the nose pin 1 in the front end 7 of the casing 5. An annular supporting plate 10 is provided around the nose pin 1, close to and inwardly of the sealing ring 9. Bearing balls 11 are provided in two annular races located one on each side of the thickened portion 4. The front race is defined by the supporting plate 10, the inner surface of the casing 5, the nose pin 1 and the front edge of the thickened portion 4, while the rear race is defined by the rear end 8 of the casing 5, the inner surface of the casing 5, the nose pin 1 and the rear edge of the thickened portion 4. By this combination, there is achieved a thrust bearing which takes up forces in all directions.

The sealing ring 9, which preferably is made of PTFE-Teflon®, is applied to the nose pin 1, which preferably is made of stainless steel, in a press fit. Since the inner diameter of the sealing ring 9 is smaller than the diameter of the nose pin 1, a so-called lip ring is obtained on which an annular ridge (not shown in FIG. 1) is formed on the front of the sealing ring 9 against the surface of the nose pin 1. The lip ring prevents undesired and foreign material from penetrating into the interior of the toothbrush. Both the supporting plate 10, which preferably is made of steel, and the sealing ring 9 are mounted in a press fit in the open front end 7 of the casing 5. Since the inner diameter of the supporting plate 10 exceeds the diameter of the nose pin 1, the supporting plate 10 does not rotate when the nose pin 1 rotates, and also the sealing ring 9 is at standstill when the nose pin 1 rotates, since the friction between the outer circumferential edge surface of the sealing ring 9 and the inner circumferential surface of the casing 5, which preferably is made of steel, is higher than that between the inner circumferential surface of the sealing ring 9 and the outer circumferential surface of the nose pin 1. The supporting plate 10 is maintained in place between the sealing ring 9 and an edge of the inside of the casing 5, as is apparent from FIG. 1. The supporting plate 10 serves as support and abutment for the bearing balls 11, which preferably are made of hardened steel. If the bearing balls 11 had been directly applied against the sealing ring 9 of Teflon ®, the axial thrust action during operation of the toothbrush would have caused recesses to form in the softer sealing ring 9 with ensuing wear. The ball bearings 11 also serve to prevent lubricant from excaping at the two ends of the gap 6.

The entire sealing and bearing arrangement, including the casing, is sealingly accommodated in a space of the same shape as the plastic cover 13 accommodating the entire toothbrush. The outer surface of the casing 5 is formed with slits in the axial direction, and the inside of the cover is provided with ridges extending in the circumferential direction. Thus, no foreign material can penetrate between the outer surface of the casing 5 and the inner surface of the cover and, consequently, neither can any such material penetrate into the interior of the casing 5 from the rear end portion thereof.

The type of watertight bearings with small bearing balls provided by the present invention is not available in the market but is altogether unique. Moreover, a press fit seal is not previously known in this context. At the tests described below, this seal has proved to be very efficient, and no trace of any foreign material has been found in the bearing space. In these tests, which were executed at different loads, the bearing device according to the invention proved to be much more durable than other types of bearings, and its durability was, furthermore, found to increase after a running-in period.

In a preferred embodiment of the invention, thirteen steel balls 11 with a diameter of 0.8 mm are arranged in each of the two races. Lubricant for the bearing is accommodated in these races and in the clearance 6 between the inner surface of the casing 5 and the central member, including the thickened portion 4 of the nose pin 1. Furthermore, the outer diameter of the sealing ring 9 is 4.5 mm, the inner diameter is 2.5 mm, and the height is 0.8 mm. The outer diameter of the supporting plate 10 is 4.5 mm, the inner diameter is 2.7 mm, and the height is 0.25 mm. The outer diameter of the casing 5 is 5.3 mm, and the inner diameter is 4.2 mm. The diameter of the nose pin 1 is 2.6 mm, the diameter of the thickened portion 4 is 3.8 mm, and the diameter of the thinner portion of the nose pin 1 closest to the rear member 3 is 2.0 mm.

At the rear member 3 of the nose pin 1, a powertransmitting means, e.g. in the form of an S-hook, a gear wheel, or a single or double universal joint, is connected to the motor adapted to rotate the nose pin 1 and usually disposed in the rear end of the toothbrush.

The tests described below concern the sealing ability and load endurance of toothbrushes equipped with the sealing and bearing arrangement according to the invention.

Sealing Test

In a sealing test of an electric toothbrush with the sealing and bearing arrangement according to the invention, the toothbrush was subjected to thrust load at different angles when resting on a horizontal, stationary pair of scales indicating the size of the load. After the toothbrush had been subjected to load for a given period of time, the sealing and bearing arrangement was tested for watertightness. The brush was placed in an upright position, a hose with an inner diameter of 8.0 mm and an outer diameter of 12.5 mm was mounted vertically on the tip of the toothbrush and filled with a water column about 20 cm high, the water level in the hose was carefully read after a given period of time, and the hose and the water column were removed.

The procedure below was used for a more accurate test of the watertightness of the inventive toothbrush. First, the toothbrush was subjected to load and was rotated for 2 min. at an angle of 45° to the supporting surface. This may be regarded as corresponding to the brushing of molars. Then, the toothbrush was connected to the above water column for 2 min., and the subsequent careful reading of the height of the water column showed that the sealing arrangement according to the invention holds absolutely thight. This test was repeated another four times in succession.

Then, the toothbrush was subjected to load at 45° to the supporting surface and stopped at a load of 1500 g. Subsequently, the brush was loaded axially and stopped at a load of 8000 g. After being connected with water as above for 2 min., the toothbrush proved to be watertight. After that, the toothbrush was in unloaded operation for 60 min., and after being connected with water for 2 min., it proved to be watertight. Then, the toothbrush was recharged for 20 h. After that, it was subjected to load (it stopped at 100 g) at 45°, connected with water for 2 min. (watertightness was established), again loaded at 45° (it stopped at 1800 g), and connected with water for 3 min. (watertightness was established).

Then, the toothbrush was subjected 13 times in succession to load at 45° and connected with water for 3 min. after each time and stopped at loads between 1900 and 2400 g. Each time, the brush proved to be watertight. After that, the brush was subjected 5 times in succession to load for 3 min., the brush being rotated all the time at an angle of 45° to the supporting surface, whereupon it was connected with water for 3 min. and each time proved to be watertight. Finally, the clearance 6 between the casing 5 and thickened portion 4 was viewed through a microscope, but no leak could be found, for which reason a toothbrush equipped with the sealing and bearing arrangement according to the invention must be regarded as extremely watertight.

Load Endurance Test

Four different toothbrushes equipped with different bearing devices were tested as to their ability to withstand load. Toothbrush A corresponds to the prior art toothbrush described above. Toothbrush B is similar to toothbrush A, but has no collar or bronze plate. Toothbrush C is similar to toothbrush B, but its thickened portion is longer in the axial direction, and there are also some differences in the design of the gear wheels in the transmission mechanism of the toothbrush. Toothbrush D is equipped with the sealing and bearing arrangement according to the invention.

In the tests, each brush was subjected to load at 45° to a horizontal, stationary supporting surface in the form of a pair of scales. Thus, the load (in grammes) at which the toothbrush stopped could be read and marked in the diagram shown in FIG. 2. Then, each toothbrush was in unloaded operation for 4 min., whereupon another load endurance test was carried out. These tests were repeated at 4-minute intervals for 84 min. The results are shown in the diagram in FIG. 2. The asterisks within parentheses (toothbrush D) indicates that the brush proper had been worn out, necessitating the mounting of a new brush for the subsequent test.

These results prove that toothbrush D equipped with the sealing and bearing arrangement according to the invention can withstand much higher loads at 45° than the other toothbrushes. Furthermore, the endurance of tooth-brush D was found to increase after a running-in period.

I claim:

1. A sealing and bearing arrangement in electric toothbrushes (13), said arrangement comprising a cylindrical, rotatable nose pin (1) which has a front member (2) on which a brush (12) is to be mounted, a rear member (3) connected to a means (14) transmitting power from a motor (3A), and a central member partly consisting of a thickened portion (4); and a hollow casing (5) which is immobile when the nose pin rotates and which coaxially encompasses the central member, including said thickened portion (4), and whose front end (7) located proximate to the front member (2) is open, while its rear end (8) located proximate to the rear member (3) encompasses the nose pin (1), there being a clearance (6) between the inner surface of the casing (5) and the central member of the nose pin (1), characterised by a sealing ring (9) for sealing against any unwanted material, said ring being arranged around the nose pin (1) in the open end (7) of the casing (5) and being immobile when the nose pin (1) rotates; an annular supporting plate (10) which is provided close to and inwardly of the sealing ring (9) towards the thickened portion (4) and which is immobile when the nose pin (1) rotates; and bearing balls (11) provided in two races, one on each side of the thickened portion (4), for taking up forces in all directions, the front race located proximate to the front member (2) being defined by the supporting plate (10), the inner surface of the casing (5), the nose pin (1) and the closest edge of the thickened portion (4), and the rear race located proximate to the rear member (3) being defined by the rear end (8) of the casing (5), the inner surface of the casing (5), the nose pin (1) and the closest edge of the thickened portion (4).

2. Sealing and bearing arrangement as claimed in claim 1, characterised in that the sealing ring (9) and the supporting plate (10) are fixed to the front end (7) of the casing (5) in a press fit.

3. Sealing and bearing arrangement as claimed in claim 1, characterised in that each race accommodates thirteen balls made of hardened steel.

4. Sealing and bearing arrangement as claimed in claim 1, characterised in that the sealing ring (9) is made of PTFE.

5. Sealing and bearing arrangement as claimed in claim 1, characterised in that the nose pin (1), the casing (5) and the supporting plate (10) are made of steel.

* * * * *